United States Patent [19]

Kaiser et al.

[11] Patent Number: 4,953,563
[45] Date of Patent: Sep. 4, 1990

[54] PROTECTIVE DISPOSABLE SHEATH FOR MUSCLE MONITOR

[76] Inventors: Howard Kaiser; Laurie A. C. Kaiser, both of 75-04 249 St., Bellerose, N.Y. 11426

[21] Appl. No.: 876,484
[22] Filed: Jun. 20, 1986
[51] Int. Cl.$^5$ .............................................. A61B 5/22
[52] U.S. Cl. .................................... 128/778; 128/780
[58] Field of Search ................ 128/778, 774, 748, 780

[56] References Cited

U.S. PATENT DOCUMENTS

| | | | |
|---|---|---|---|
| 2,541,520 | 2/1951 | Kegel | 128/778 |
| 3,752,150 | 8/1973 | Harris | 128/778 |
| 3,926,178 | 12/1975 | Feldzamen | 128/778 |
| 4,216,783 | 8/1980 | Kaiser et al. | 128/748 X |
| 4,476,880 | 10/1984 | Glem et al. | 128/778 |

Primary Examiner—Angela D. Sykes
Attorney, Agent, or Firm—Cushman, Darby & Cushman

[57] ABSTRACT

A generally funnel-shaped protective disposable sheath is provided for use with a muscle monitor of the kind including a compressible-expansible elongated bulb insertable into a body cavity and a generally annular flange of greater diameter than the bulb adjacent one end of the bulb for limiting the extent of penetration of the bulb into the body cavity. The sheath is made of flexible elastomeric material and includes an anterior end portion which is adapted to fit over the bulb. The anterior portion is of elongated tubular configuration having a closed free end and an opposite end which is open and merges into a generally cup-shaped posterior portion of enlarged diameter adapted to overlie that surface of the muscle monitor flange which faces the bulb.

4 Claims, 3 Drawing Sheets

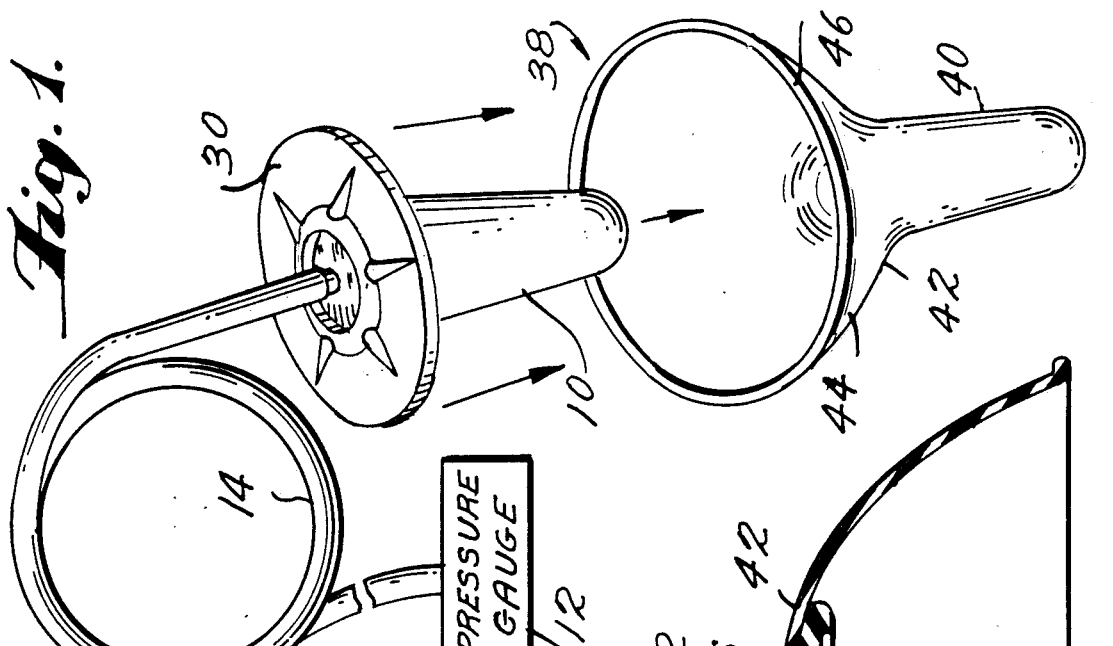
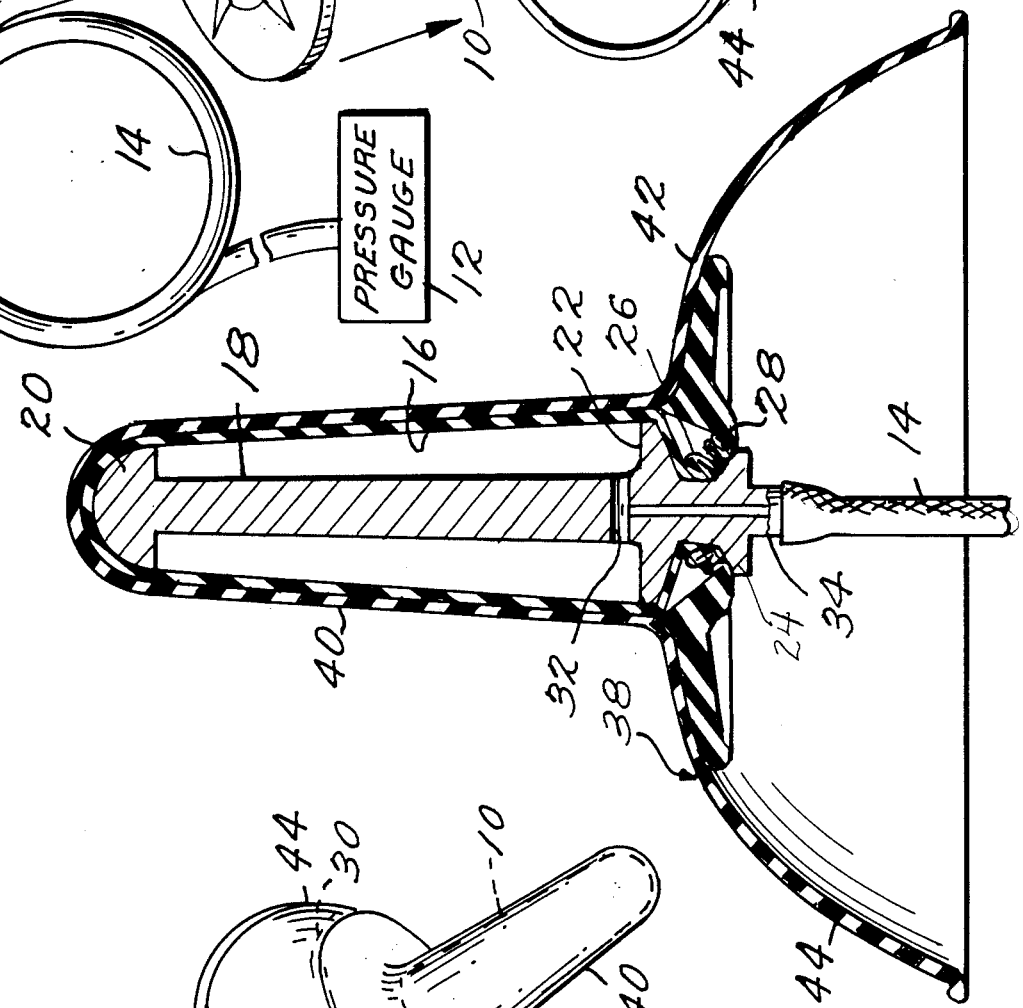
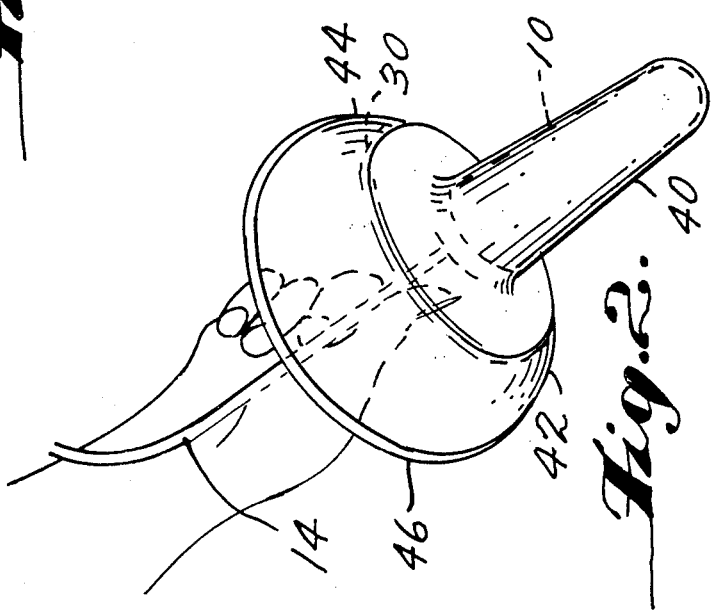

PROTECTIVE DISPOSABLE SHEATH FOR MUSCLE MONITOR

This invention relates to a disposable sheath for a muscle monitor of the kind which is insertable into a body cavity for the purpose of measuring the strength of contractile muscles.

BACKGROUND AND SUMMARY OF THE INVENTION

U.S. Pat. Nos. 2,507,858, 2,541,520 and 4,216,783 disclose devices for measuring the strength of contractile muscles. The latter patent is particularly concerned with providing a visual indication of the strength of vaginal muscles. The basic construction of such a muscle monitor includes a hollow, flexible, compressible bulb assembly insertable into the vagina and a flexible tube connecting the bulb with a gauge for measuring the increase in internal air pressure which results from the patient's contraction on the bulb. The monitor is useful as a biofeedback device for measuring the strength of the pubococcygeus (PC) muscle for the purpose of aiding the user to increase the degree and strength of control exercised over that muscle.

In accordance with the present invention, there is provided a disposable sheath or shield which can be placed over the bulb portion of the monitor prior to use and subsequently discarded. The use of the sheath is particularly advantageous to the doctor or technician in that it allows the doctor or technician to measure and record PC muscle strength as a routine office procedure during patient visits. As the disposable sheath serves as a protective barrier between the vaginal tissues and the parts of the monitor which would otherwise come in contact with the vaginal tissues, it is not necessary to sterilize or replace those parts of the device after each use.

The sheath is made of thin latex or other flexible, slightly elastic material and is generally complementary in size and shape to the bulb and adjacent portion of the bulb. It fits the exterior of the bulb snugly so as not to be dislodged during use but it is easily removed when desired.

BRIEF DESCRIPTION OF THE DRAWING

FIG. 1 is a perspective view of a contractile muscle measuring monitor being fitted with a disposable sheath embodying the principles of the present invention;

FIG. 2 is a perspective view of the sheath and bulb portion of the assembly of FIG. 1 with the sheath in place; and FIG. 3 is an axial sectional view of the bulb portion and sheath.

DETAILED DESCRIPTION

FIG. 1 illustrates a muscle monitor which includes a hollow flexible bulb 10, a gauge 12 for measuring air pressure and a flexible tube 14 connecting the interior of the bulb 10 to the gauge 12. The bulb, tube and gauge form a closed pneumatic system so that compression of the bulb 10 by an exterior force increases the pressure of the air in the bulb, such pressure increase resulting in a visual reading by the gauge. The gauge may be a simple mechanical gauge or it may be incorporated in any of a variety of electronic devices designed to give visual, audio or printed indications of pressure. The bulb assembly 10 may comprise a soft flexible elastomeric cover 16 fitted over a central rigid or semi-rigid post 18 or plastics material or metal. The post 18 has a hemispherical outer end 20 of enlarged cross section relative to the body of the post and at its inner end are two radial shoulders of flanges 22 and 24. The cover 16, which has a closed outer end, is lightly stretched over the outer end 20 of the post 18 and is sealed to the inner end of the post 18 by an elastic O-ring 26. An integral reinforcing bead 28 on the mouth of the cover 16 prevents the sheath 18 from tearing as it is stretched over the flange 22. A soft rubber circular flange 30 having a central hole therein is releasably attached to the inner end of the post 18 by pressing the flange 30 into the space between the flanges 22 and 24. The diameter of the flange 30 is substantially greater than the diameter of the cover 16. An air passage 32 extends from the space between the post 18 and the sheath 16 through the core of the post 18 to a connection 34 over which the flexible air tube 14 is forced. The precise structure of the bulb 10 and the flange 30 are of no importance to the present invention; the illustrated parts are merely exemplary.

According to the principles of the present invention, the bulb assembly 10, prior to insertion into the vagina, is fitted glove-like with an external protective sheath 38 which prevents direct contact of the monitor with the internal and external surfaces of the vagina. To this end the sheath 38 is generally funnel-shaped and includes an anterior end portion 40 which is contoured to the size and shape of the bulb 10, generally frustoconical in the illustrated embodiment, and a cup-shaped posterior portion 42 of enlarged diameter contoured to overlie the surface of the flange 30 which faces the bulb 10. Preferably the cup-shaped portion 42 extends axially beyond the flange 30 so as to form a skirt 44 encircling the flange 30. As illustrated in FIG. 2 the skirt 44 surrounds the fingers of the doctor or technician when the monitor is hand-held by grasping the tube 14 near its connection with the bulb 10, thereby preventing direct contact of the fingers with the patient. The open end of the skirt 44 terminates in a circumferential reinforcing bead 46.

In use of the monitor the bulb assembly 10 is inserted into the vagina to the extent permitted by the soft rubber flange 30, the latter contacting the external surfaces of the vagina thereby aiding in locating the bulb assembly 10 in the proper position within the vagina. The precise shape of the bulb assembly 10 is not critical although an elongated frusto-conical shape as shown is particularly suitable. Upon contraction and relaxation of the vaginal muscles, particularly the PC muscle, the bulb assembly 10 is slightly compressed and released in radial directions and the resulting increase or decrease in air pressure within the assembly 10 is transmitted through the tube 14 to the gauge 12.

The protective sheath 36 is removed from the monitor by grasping the skirt 44 with the fingers of one hand, while holding the monitor with the other hand, and stripping the sheath, inside out, from the flange 30 and bulb 10.

What is claimed is:

1. A generally funnel-shaped protective disposable sheath for use with a muscle monitor of the kind including a compressible-expansible elongated blub insertable into a body cavity and a generally annular flange of greater diameter than the bulb adjacent one end of the bulb for limiting the extent of penetration of the bulb into the body cavity, said sheath being made of flexible elastomeric material and including a posterior end portion and an anterior end portion adapted to fit over the bulb, said anterior portion being of elongated tubular configuration having a closed free end, the opposite end of said anterior portion being open and merging in an axial direction into a generally cup-shaped posterior portion of enlarged diameter adapted to overlie that surface of a muscle monitor flange which faces the bulb of the monitor, said cup-shaped posterior portion diverging outwardly along essentially its entire length and terminating in a skirt having an open end of maximum diameter.

2. A sheath as in claim 1 wherein said posterior end portion of said sheath is elongated in the axial direction so as to form a skirt which extends rearwardly of the muscle monitor flange when said sheath overlies a muscle monitor.

3. In a muscle monitor of the kind including a compressible-expansible elongated bulb insertable into a body cavity, a generally annular flange of greater diameter than the bulb attached to and adjacent one end of the bulb, said flange having a rear surface facing away from the bulb and a front surface limiting the extent of penetration of the bulb into the body cavity, the improvement comprising a removable, generally funnel-shaped, external protective sheath, the sheath being made of flexible elastomeric material and including an anterior end portion of elongated tubular configuration complementary to the bulb and having an outer closed end and an opposite end, the anterior end portion overlying and contacting the exterior of the bulb, the opposite end of the anterior portion being open and merging in an axial outward direction into a generally cup-shaped posterior portion of enlarged diameter which diverges radially outward and overlies and contacts the surface of the flange which faces the bulb, said cup-shaped posterior portion of the sheath extending rearwardly of the monitor flange and forming a skirt around the flange, said skirt being out of contact with the rear surface of the monitor flange.

4. A muscle monitor comprising: a radially compressible-expansible elongated bulb insertable into a body cavity, said bulb having an anterior end and a posterior end and a smooth continuous outer surface; a generally annular flange of greater diameter than the bulb located at the posterior end of the bulb; said flange having a rear surface facing away from the bulb and a front surface facing the bulb; a removable discardable protective sheath overlying the bulb and the front surface of the flange, the sheath being made of thin flexible sheet material and including an anterior end portion of elongated tubular configuration complementary to the bulb and having an outer closed end and an opposite end, said opposite end being open and merging in an axial outward direction into a posterior portion of larger diameter, said posterior portion overlying the front surface of said flange and being out of contact with the rear surface of said flange.

* * * * *